United States Patent [19]
Fleer et al.

[11] Patent Number: 5,821,038
[45] Date of Patent: Oct. 13, 1998

[54] YEAST WITH MODIFIED PERMEABILITY

[75] Inventors: Reinhard Fleer, Bures Sur Yvette; Daniel Scherman; Christophe Marcireau, both of Paris, all of France

[73] Assignee: Rhone-Poulenc Rorer S.A., Antony Cedex, France

[21] Appl. No.: 809,543

[22] PCT Filed: Sep. 22, 1995

[86] PCT No.: PCT/FR95/10226

§ 371 Date: Mar. 20, 1997

§ 102(e) Date: Mar. 20, 1997

[87] PCT Pub. No.: WO96/10082

PCT Pub. Date: Apr. 4, 1996

[30] Foreign Application Priority Data

Sep. 27, 1994 [FR] France .................................. 94 11509

[51] Int. Cl.$^6$ ............................. C12Q 1/02; C12N 15/00; C12N 1/16; C12N 1/18
[52] U.S. Cl. ...................... 435/4; 435/172.1; 435/255.1; 435/255.2; 435/255.5; 435/255.6
[58] Field of Search ................................ 435/4, 6, 254.2, 435/254.21, 254.23, 255.2, 255.1, 255.4, 255.5, 255.6, 172.1

[56] References Cited

PUBLICATIONS

Lees et al. (1992) Genetics and molecular biology of the genes functioning late in the sterol biosynthetic pathway in Saccharomyces. ACS Symp. Ser. 497:246–259, 1992.

Roemer et al. (1933) SN1 and KRE6 define a pair of functional homologs encoding putative membrane proteins involved in beta–glucan synthesis. Mol. Cell. Biol. 13:4039–4048, Jul. 1993.

Lee et al. (1993) A pair of functionally redundant yeast genes (PPZ1 and PPZ2) encoding type 1–related protein phosphatases function within the PKC1–mediated pathway. Mol. Cell. Biol. 13:5843–5853, Sep. 1993.

Nakanishi–Shindo (1993) Structure of the N–linked oligosaccharides that show the complete loss of alpha–1, 6–polymannose outer chain from och1, och1 mnn1, and och1 mnn1 alg3 mutanta of *Saccharomyces cerevisiae*. J. Biol. Chem. 268:26338–26345, Dec. 1993.

*Primary Examiner*—George C. Elliott
*Assistant Examiner*—Robert Schwartzman

[57] ABSTRACT

The present invention relates to a modified yeast wherein at least two of the genes controlling the cellular permeability of said yeast are modified, said modifications having an additive or synergic effect. It also relates to a method for the preparation of said yeast as well as to its utilizations.

13 Claims, 10 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

TTACTTTCGA TTTAAGTTTT ACATAATTTA AAA        33

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

GGCCTGCTCA TGAACGTGCT ATCTT        25

YEAST WITH MODIFIED PERMEABILITY

This application is a 371 of PCT/FR95/01226 filed Sep. 22, 1995.

The present invention relates to modified yeasts having a cellular permeability not conforming to the original one, induced by genetic mutation.

Yeast is a model of eukaryotic cells and an excellent tool for studying the metabolic pathways, the cell cycle, their respective regulatory systems, the isolation of genes, the production of heterologous proteins and the like. Yeast may also be used for the biotransformation of molecules of interest or for the discovery of biologically active compounds by in vivo screening. The latter applications require the penetration of xenobiotics inside the yeast cells.

The penetration of these molecules, like their concentration, inside the yeast cells depends on different parameters regulating cell "permeability". These different parameters act mainly at three different levels in yeast, its cell wall, its plasma membrane and its detoxification mechanisms.

Thus, for a molecule to penetrate inside yeast cells and to undergo biotransformation therein or to exert its biological effect therein in the case of a screening, it has to cross the wall (essentially composed of glucans, mannoproteins and chitins) and the plasma membrane (composed of sterols, phospholipids and proteins), two biological barriers which may weakly or strongly block its penetration. To maintain a high concentration inside the cell, it should not undergo detoxification, for example by reexpulsion towards the external medium or by metabolism inside the cell.

The literature reports a whole series of genes involved in the biosynthesis, the constitution and/or the integrity of the wall, the membrane and at the level of the detoxification systems.

Various genes are involved in the synthesis of the wall, such as the series of genes comprising KRE (Hutchins, 1983; Boone, 1990; Meader, 1990; Hill, 1992; Roemer, 1991; Brown, 1993; Klis, 1994), KTR (Lussier, 1993; Klis, 1994) and MNN (Kanik, 1990; Klis, 1994; Ballou, 1982). It has been possible to isolate different wall mutants such as the mutants csd, chs, och, skn1, pmr1, pmt1, erd1, vgr1, vgr4, cal3, shc1, pkc1, bck1, mkk1, mkk2, mpk1, ppz1, ppz2, pmi1 (Klis, 1994). The genes DHS1 (Lee, 1994), SRB1 (Stateva, 1991), as well as the genes involved in the signalling pathway for protein kinase C which negatively controls the degradation of the wall by different glucanases such as BGL2 (Shimizu, 1994; Klis, 1994), are more particularly involved in the integrity of this wall.

The identity of a whole set of genes involved in the biosynthesis of ergosterol, which is a predominant form of fungal sterols, has also been identified. Sterols are membrane constituents. By way of representative of these genes, there may be mentioned more particularly the genes ERG10 (Dequin, 1988), ERG11 and ERG13 (Servouse, 1984), HMG1 and RMG2 (Basson, 1986), ERG12 (Oulmouden, 1988), ERG8 (Tsay, 1991), ERG19 (Mons, 1984), ID11 and ERG20 (Anderson, 1989), ERG9 (Fegueur, 1991), ERG1 (Hoegenauer, 1991), ERG18 (Karst, 1977), ERG7 and ERG17 (Karst, 1977), ERG16 (Kalb, 1987), ERG24 (Marcireau, 1992), ERG6 (Hardwick, 1994), ERG2 (Ashman, 1991), ERG3 (Arthington, 1991), ERG5 (Molzhan, 1972), ERG4 (Lai, 1994). The phospholipids are also membrane constituents. Various genes involved in the synthesis of phospholipids have been identified, such as CHO1 (Kiyono, 1987), CHO2 (Kodaki, 1991), PEM2 (Kodaki, 1987), CK11 (Hosaka, 1989), CCT1 (Tsukagoshi, 1987), EPT1 and CPT1 (Hjelmstad, 1991), INO1 (Dean-Johnson, 1989), PIS1 (Nikawa, 1987) and the like. Likewise, various genes involved in the synthesis of fatty acids have been identified. Acetyl-CoA carboxylase (ACC1 gene (Al-Fell, 1992)) makes it possible to produce malonyl CoA which will be used by fatty acid synthase (the genes FAS1 (Schwezer, 1986) and FAS2 (Mohamed, 1990)) to give fatty acids. The unsaturation(s) will be introduced by virtue of the action of the fatty acid desaturase encoded by the OLE1 gene (Stukey, 1990).

As regards more particularly the detoxification phenomenon, it has been possible to demonstrate several mechanisms in yeast. In particular, the neutralization of the free radical groups depends on the expression of the SNQ3 gene (Moye-Rowley, 1989). Moreover, the yeast has proteins capable of expelling, into the external medium, xenobiotics which have penetrated into the cell or endogenous compounds. Some, such as SNQ1 (Kanawaza, 1988) have a fairly strict transport specificity, on the other hand, others such as PDR5 (Leppert, 1990), SNQ2 (Servos, 1993) and STE6 (Kuchler, 1989) have a weak specificity and can therefore transport a large number of molecules. It has been possible to identify various genes controlling the expression of these proteins, such as the genes PDR1 (Meyers, 1992), PDR3, PDR4, PDR7, PDR9, PDR11 (Dexter, 1994). It has been possible to identify other genes such as PDR2 and PDR6 (Balzi, 1991) which are involved in these mechanisms, but their functions remain poorly understood for the moment.

It should be noted that the proteins encoded by the SNQ2, STE6, PDR5 genes resemble, by virtue of their composition and their structure, the p-glycoproteins which are strongly expressed in numerous tumour cells which have become resistant to cytotoxic agents. These proteins are commonly called MDR (multiple drug resistance) pumps.

The regulation of the various parameters acting at the level of this detoxification mechanism and, more generally, indirectly or directly controlling cellular permeability, would-be particularly valuable from a therapeutic point of view.

In particular, it would be particularly advantageous to be able to have a yeast exhibiting an enhanced permeability for the purposes of screening biologically active products or of studying cell metabolisms and/or behaviours. Indeed, in this type of yeast, the intracellular concentration of a compound would be increased compared with normal yeasts, for the same concentration of product in the external medium. This increased intracellular concentration would allow an easier detection of the activity of the product in the context of the screening and discovery of active compounds (Kirsch 1993, Hara 1993). It would also be advantageous for obtaining a greater transformation of a substrate during a biocatalysis (Yasubaki 1992) or for examining the metabolism of a compound, using, for example, yeasts expressing human cytochromes p450 (Renaud 1990).

Unexpectedly, the Applicant has demonstrated that the combination, in a yeast, of at least two mutations at the level of at least two of the abovementioned genes and each controlling permeability, at different levels or otherwise, positively affected the permeability of the said yeast. This results in an increased gain in permeability. This gain corresponds at least to that derived from the superposition of the respective effects.induced by each of the mutations, and is more preferably considerably greater than it. An addition and more preferably an amplification of the respective effects, that is to say a synergy, are advantageously observed.

More precisely, the present invention relates to a modified yeast in which at least two of the genes controlling the cellular permeability of the said yeast are modified, the said modifications having an additive or synergic effect.

The genes affected in their function, within the framework of the present invention, can control the cellular permeability at identical or different levels. However, it may be advantageous to alter the activity of the genes affecting the cellular permeability at different levels.

These modified genes are chosen from the genes which play a role in the constitution, the biosynthesis and/or the integrity of the wall or of the plasma membrane and the genes involved in the mechanisms of detoxification or of export of endogenous compounds.

For the purposes of the present invention, modified gene is understood to mean a gene which has been made partially or totally incapable of encoding its natural protein. The incapacity of the said genes to encode their natural proteins may manifest itself either by the production of an inactive protein because of structural or conformational modifications, or by the absence of production, or by the production of the natural protein at a reduced level or according to a desired mode of regulation or alternatively by the production of a mutant having a modified activity spectrum. In the latter case, this may be a modification of the type comprising an increase or a decrease in specific activity, but also a change at the level of its substrate or product specificity.

This gene modification is induced by one or more genetic modifications.

Genetic modification should be understood to mean more particularly any suppression, substitution, deletion, insertion or addition of one or more bases into the gene(s) considered. Such modifications may be obtained in vitro (on the isolated DNA) or in situ, for example, by means of genetic engineering techniques, or alternatively by exposing the said microorganisms to a treatment by means of mutagenic agents. As mutagenic agents, there may be mentioned, for example, physical agents such as energetic radiation (X rays, gamma rays, ultra violet rays and the like), or chemical agents capable of reacting with different functional groups of the DNA bases, and for example alkylating agents [ethyl methanesulphonate (EMS), N-methyl-N'-nitro-N-nitrosoguanidine, N-nitroquinoline-1-oxide (NQO) and the like], dialkylating agents, intercalating agents and the like. Deletion is understood to mean any partial or total suppression of the gene considered. This may be especially a part of the region encoding the said proteins, and/or all or part of the promoter region for transcription, translation or alternatively the transcript.

The said genetic modification(s) may also be obtained by gene disruption, for example according to the procedure initially described by Rothstein (Rothstein, 1983) or advantageously by double homologous recombination. In this case, the coding sequence will be preferably partly or totally perturbed so as to allow, where appropriate, the replacement, by homologous recombination, of the wild-type genomic sequence by a nonfunctional, mutant sequence and/or by a selectable marker.

The said genetic modification(s) may be localized in the coding gene or outside the coding region, for example in the regions responsible.for the expression and/or transcriptional or post-transcriptional regulation of the said genes.

Moreover, certain alterations such as point mutations are by nature capable of being corrected or attenuated by cellular mechanisms, for example during the replication of the DNA preceding cell division. Such genetic alterations are then of a limited interest at the industrial level since the phenotypic properties which result therefrom are not perfectly stable. The Applicant used a process which makes it possible to prepare yeasts having at least two genetic modifications at the level of two respective genes, the said modification(s) being segregationally stable and/or nonreversible. This process indeed allows the modification of multiple genes using the same selectable marker.

Preferably, the yeasts according to the invention exhibit several segregationally stable genetic modifications. Still according to a preferred mode, the genetic modifications are nonreversible.

Of course, the subject of the present invention is not limited to yeasts comprising only two inactivated genes. The modified yeasts according to the invention may contain a considerably larger number of mutated genes.

The yeasts according to the invention may be obtained by modifying at least two genes chosen from the genes which play a role at the level of the constitution, the biosynthesis and/or the integrity of the wall and/or of the plasma membrane, and/or the genes involved in the mechanisms of detoxification or of export of endogenous compounds, their homologues or derivatives.

For the purposes of the present invention, derivative is understood to mean any sequence obtained by modification and encoding a product which conserves at least one of the biological properties of the natural protein (trophic and/or differentiator effect). Modification should be understood to mean any mutation, substitution, deletion, addition or modification of a genetic and/or chemical nature. The derivatives, for the purposes of the invention, may also be obtained by hybridization from nucleic acid libraries, using, as probe, the native sequence or a fragment thereof.

Among the preferred derivatives, there may be mentioned more particularly the natural variants, the molecules in which one or more residues have been substituted, the derivatives obtained by deletion of the regions which play little or no role in the interaction with the binding sites considered or expressing an undesirable activity, and the derivatives comprising, compared with the native sequence, additional residues.

Homologous gene is understood to mean, within the framework of the present invention, a gene fulfilling a function identical or equivalent to that of a gene expressly designated and isolated from a same or another microorganism.

More preferably, the genes capable of being modified within the framework of the present invention are selected among:

the genes which play a role in the synthesis of the cell wall or in maintaining its integrity. As representative of these genes, there may be mentioned particularly the genes XRE, KTR, MN, CSD, CHS, OCH, SKN1, PMR1, PMT1, ERD1, VGR1, VGR4, CAL3, SHC1, DHS1, SRB1, PKC1, BCK1, MKK1, MKK2, MPK1, PPZ1, PPZ2, PMI1 and BGL2, the genes which play a role at the level of the synthesis of the cell wall by participating especially in the synthesis of sterols, constituents of the cell membranes, and more particularly the genes ERG10, ERG11, ERG13, RMG1, RMG2, ERG12, ERG8, ERG19, IDI1, ERG20, ERG9, ERG1, ERG18, ERG7, ERG17, ERG16, ERG24, ERG6, ERG2, ERG3, ERG5 and ERG4, the genes involved in the mechanisms of detoxification or of export of endogenous compounds developed by the cell, such as the genes SNQ1, SNQ2, SNQ3, STE6, PDR1, PDR2, PDR3, PDR4, PDR6, PDR7, PDR9 and PDR11 and their homologues.

The yeast cells capable of being modified according to the invention may be chosen from the genera Kluyveromyces, Saccharomyces, Pichia, Hansenula, Candida, Schizosaccharomyces and analogues thereof and more preferably between the genera Kluyveromyces, Saccharomyces. The preferred species of Saccharomyces is S. Cerevisiae.

According to a specific embodiment of the invention, the mutations may be performed at the level of at least two genes controlling the permeability of the yeasts at different levels. For example, this may be a yeast combining, with an inactivation of a gene involved in the mechanisms of detoxification, an inactivation of a gene involved in the biosynthesis and/or the constitution either of the plasma membrane or of the wall of the said yeast.

By way of illustration of the claimed yeasts, there may be mentioned more particularly yeasts in which the PDR1, PDR5, SNQ2, ERG6 genes have been modified as in the yCM61 strain, which is described in the examples below.

In this specific case, a particularly advantageous synergy is observed. Such a yeast has a considerably enhanced permeability which results in a hypersensitivity to cytotoxic products having intracellular targets and different mechanisms of action (see examples).

The subject of the invention is also a process for the preparation of a genetically modified yeast and its use. Preferably, the process of the invention consists in replacing the chromosomal genes considered by a modified version in vitro.

The present invention relates, in general, to any use of a yeast according to the invention for the purposes of penetration of a compound into the said yeast. The yeasts exhibiting an enhanced permeability according to the invention prove to be most particularly advantageous for the discovery of biologically active products in microbiological screens (Kirsch 1993, Hara 1993). Moreover, they are of interest in biocatalysis (Yabusaki 1992) or as model for studying metabolism, for understanding cell behaviour and for toxicological studies.

The present invention will be described more fully with the aid of the following figures and examples which should be considered as illustrative and nonlimiting.

GENERAL CLONING TECHNIQUES

The methods conventionally used in molecular biology, such as preparative extractions of plasmid DNA, centrifugation of plasmid DNA in caesium chloride gradient, agarose or acrylamide gel electrophoresis, purification of DNA fragments by electroelution, extractions of proteins with phenol or with phenol-chloroform, ethanol or isopropanol precipitation of DNA in saline medium, transformation in *Escherichia coli,* and the like, are well known to persons skilled in the art and are widely described in the literature [Maniatis T. et coll., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The restriction enzymes were provided by the New England Biolabs (Biolabs), Bethesda Research Laboratories (BRL) or Amersham and are used according to the recommendations of the suppliers.

The pBR322- and pUC-type plasmids and the phages of the M13 series are of commercial origin (Bethesda Research Laboratories). The pIC-type plasmids have been described by Marsh (Marsh, 1984).

For the ligations, the DNA fragments are separated according to their size by agarose or acrylamide gel electrophoresis, extracted with phenol or with a phenol/chloroform mixture, precipitated with ethanol and then incubated in the presence of T4 phage DNA ligase (Biolabs) according to the recommendations of the supplier.

The filling of the protruding 5' ends is performed with the Klenow fragment of *E. coli* DNA polymerase I (Biolabs) according to the specifications of the supplier. The destruction of the protruding 3' ends is performed in the presence of the T4 phage DNA polymerase (Biolabs) used according to the recommendations of the manufacturer.

The oligodeoxynucleotides are chemically synthesized according to the phosphoramidite method using β-cyanoethyl protective groups (Sinha 1984). After synthesis, the protective groups are removed by treatment with ammonium hydroxide and two butanol precipitations make it possible to purify and concentrate the oligodeoxynucleotides (Sawadogo, 1991). The DNA concentration is determined by measuring the optical density at 260 nm.

The transformations of *S. cerevisiae* with the DNA of the plasmids for expression of the proteins of the present invention are performed by any technique known to persons skilled in the art, and of which an example is given in the text.

The yeast strains used in the examples belong to the species *Saccharomyces cerevisiae.*

The yeast strains of the present invention are cultured in Erlenmeyer flasks at 28° C. in rich medium (YPG: 1% yeast extract, 1% Bactopeptone, 2% glucose) or a minimum medium (YNB: 0.67% Yeast Nitrogen Base (difco) without amino acids, 2% glucose) with constant stirring. The minimum medium is supplemented with base and with amino acid, where appropriate in an amount of 50 mg/L.

EXAMPLE 1

Preparation of the strains possessing inactivated ERG4, PDR1 or ERG4 and PDR1.

1) Preparation of the plasmids which make it possible to carry out multiple gene disruptions with the elimination of the selectable marker.

Figure 1:
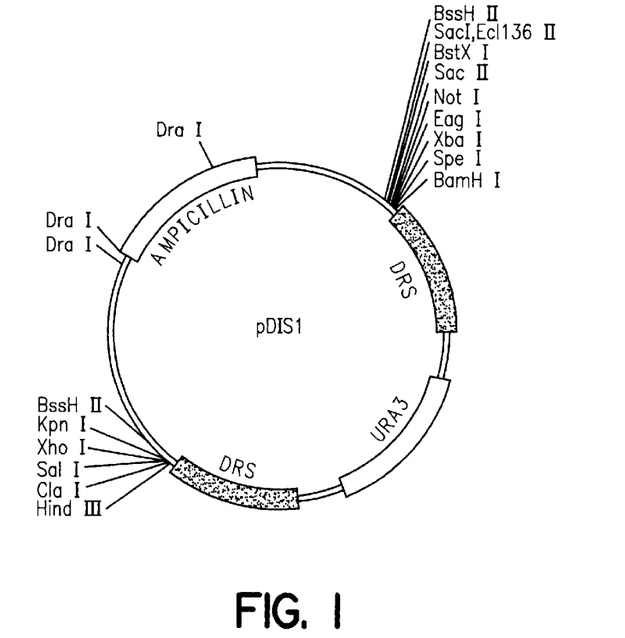
FIG. 1: Plasmid pDIS1

The plasmid Bluescript II (ks⁻) is digested with DraI. The different restriction fragments are separated by electrophoresis on a 0.8% agarose gel. The 692 bp fragment corresponding to a part of the AMP$^R$ gene is then electroeluted and purified by an extraction with a phenol-chloroform mixture. This fragment is ligated into the plasmid Bluescript II (ks⁻) previously digested with SmaI. After transformation of *E. coli* and analysis of the plasmids, only the plasmids having the inserted fragment are selected (the plasmid obtained is called pDisIdrs). The plasmid pDisIdrs is digested with EcoRV and ligated with the DraI-DraI fragment of 692 bp described above. After transformation of E. coli and analysis of the plasmids, only the plasmids having the inserted fragment as a direct repeat with the preceding one are selected (production of the plasmid pDisI2drs). The plasmid pCXJ1 (Chen 1987) having the URA3 gene is digested with EcoR1. The different restriction fragments are separated by electrophoresis on a 0.8% agarose gel. The 1282 bp fragment is then electroeluted and purified by extraction with a phenol-chloroform mixture. This fragment is ligated into the plasmid pDisI2drs previously digested with EcoR1. After transformation of E. coli and analysis of the plasmids, only the plasmid having the inserted EcoR1-EcoR1 URA3 fragment are selected. This plasmid is called pDIS1 (cf. FIG. 1).

Figure 2:
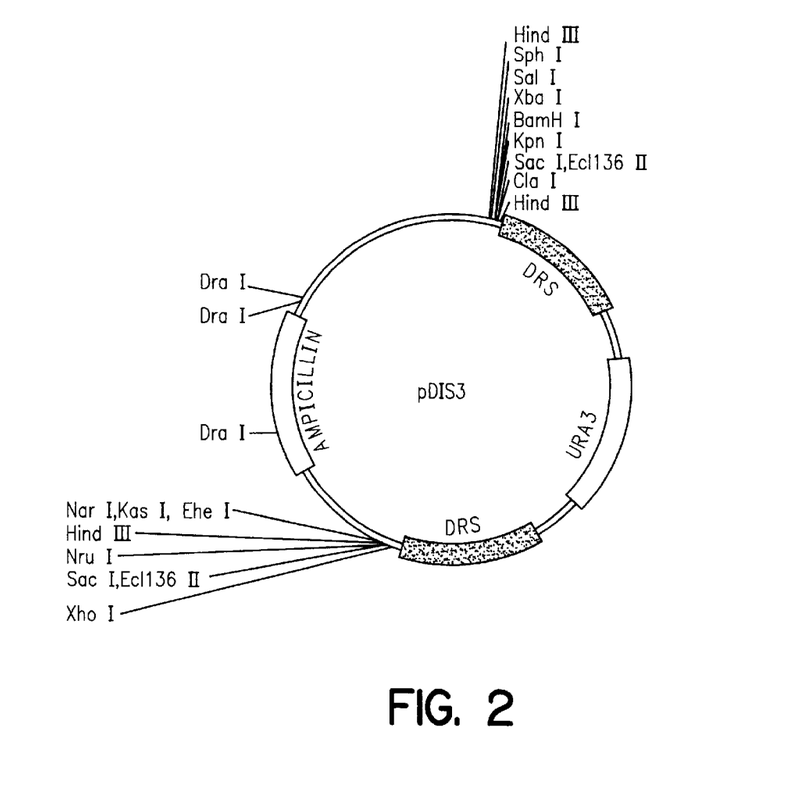
FIG. 2: Plasmid pDIS3
Figure 3:
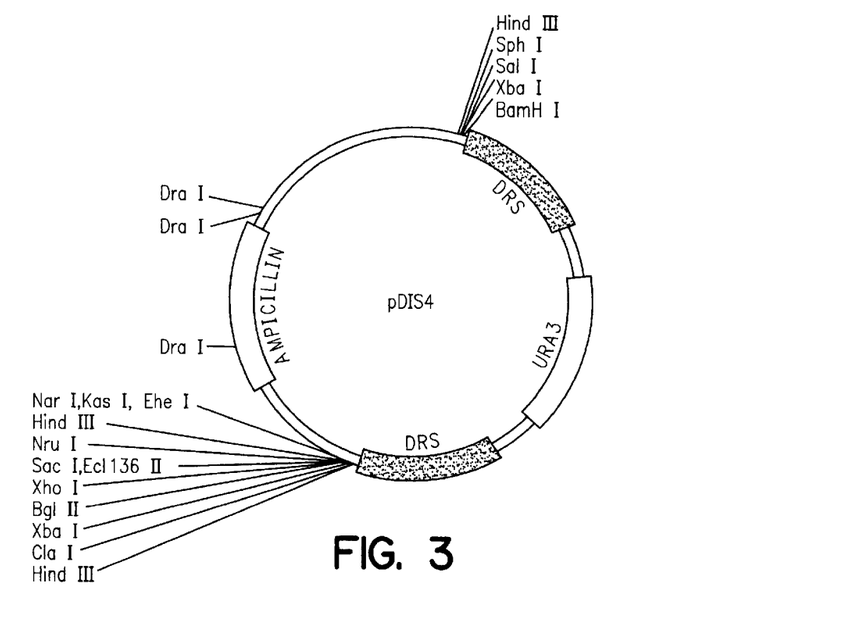
FIG. 3: Plasmid pDIS4

The plasmid pDIS1 is digested with ClaI and BamHI. The different restriction fragments are separated by electrophoresis on a 0.8% agarose gel. The 2702 bp fragment carrying the URA3 gene flanked by two direct repeat sequences is then electroeluted and purified by an extraction with a phenol-chloroform. mixture. This fragment is ligated into the plasmid pIC20H digested, on the one hand, with ClaI and BamHI and, on the other hand, with ClaI and BglII. The new plasmids having ligated this 2702 bp fragment, respectively called pDIS3 (cf. FIG. 2) and pDIS4 (cf. FIG. 3) are obtained after transformation of E. coli.

2) Production of the constructs which allow the disruption of the ERG4, PDR1 and ERG4-PDR1 genes.

a) Construct allowing the disruption of the ERG4 gene

Figure 4:
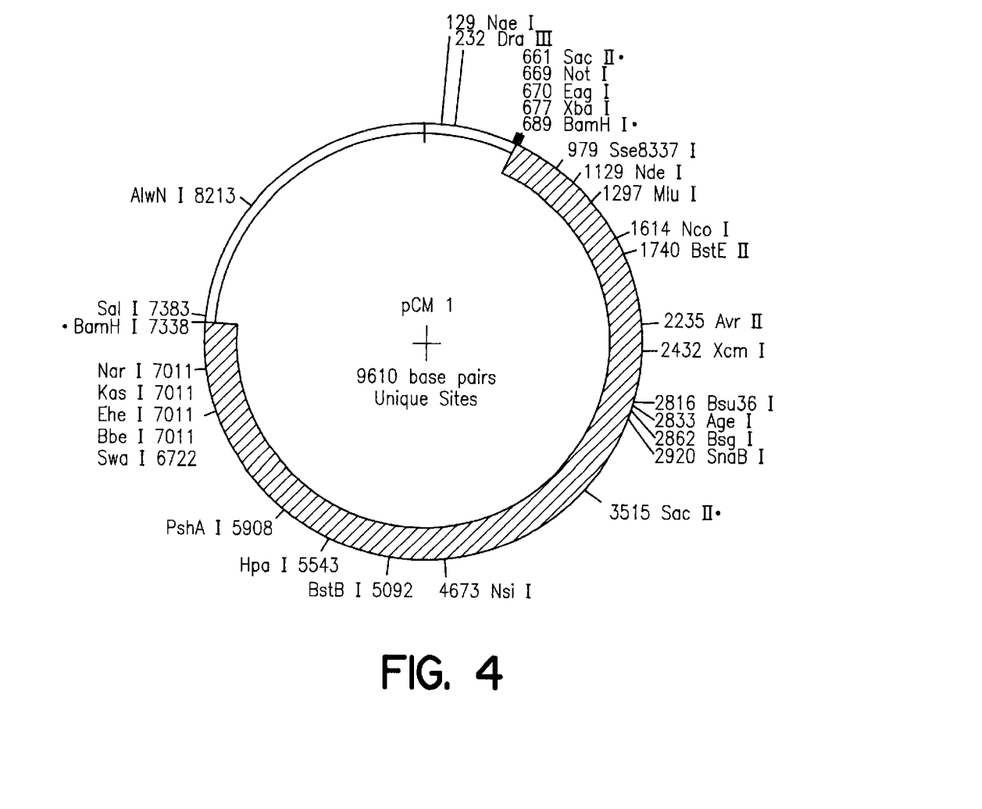
FIG. 4: Plasmid pCM1
Figure 5:
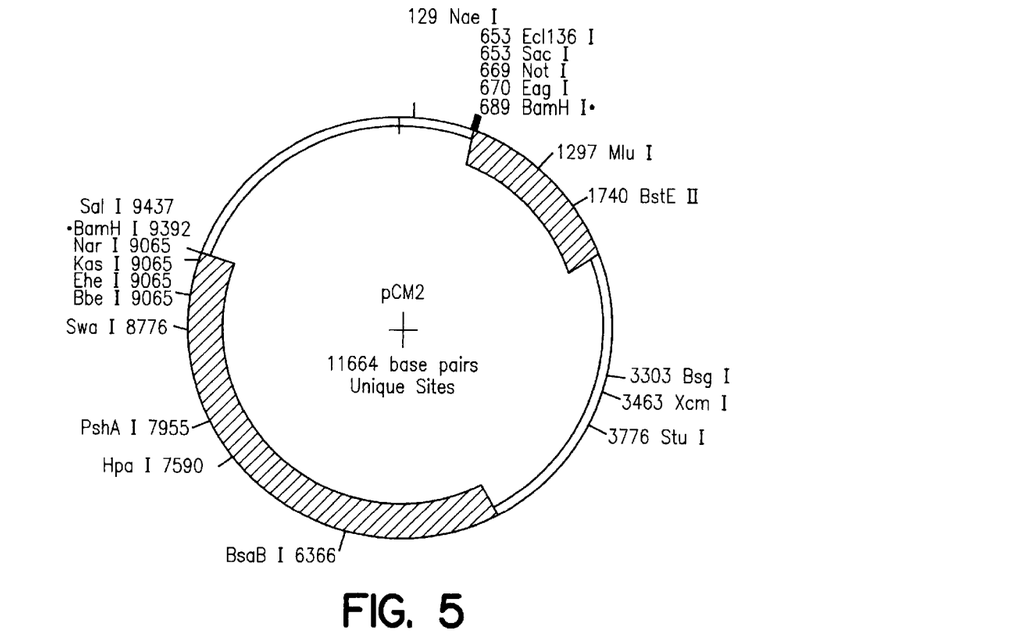
FIG. 5: Plasmid pCM2

The 6670 bp BamH1-BamHI fragment of the plasmid pA-B6.5 (Balzi 1987), whose sequence is deposited at the EMBL data bank under the reference S58126, is ligated into the plasmid Bluescript II (ks⁻) preferably digested with BamHI. This DNA fragment comprises, inter alia, the ORFs corresponding to the ERG4 and PDR1 genes. After transformation of E. coli, the plasmid possessing the insert is selected and called pCM1 (cf. FIG. 4). The plasmid pDIS4 is digested with XbaI and Ecl136II. The different restriction fragments are separated by electrophoresis on a 0.8% agarose gel. The 2726 bp fragment is then electroeluted and purified by extraction with a phenol-chloroform mixture. The plasmid pCM1 is digested with AvrII and SnaBI so as to eliminate part of the ERG4 ORF which will be replaced by the disruption cassette. The different restriction fragments are separated by electrophoresis on a 0.8% agarose gel. The 8925 bp fragment is then electroeluted and purified by extraction with a phenol-chloroform mixture. The two fragments thus prepared are ligated together. After transformation of E. coli, the plasmid allowing the disruption of the ERG4 gene is prepared. This new plasmid is called pCM2 (cf. FIG. 5). It is finally digested with SacI and SalI. The linear fragment thus obtained is electroeluted and purified by extraction with a phenol-chloroform mixture, for the purpose of the transformation allowing the disruption of the ERG4 gene.

b) Construct allowing the disruption of the PDR1 and ERG4 genes

Figure 6:
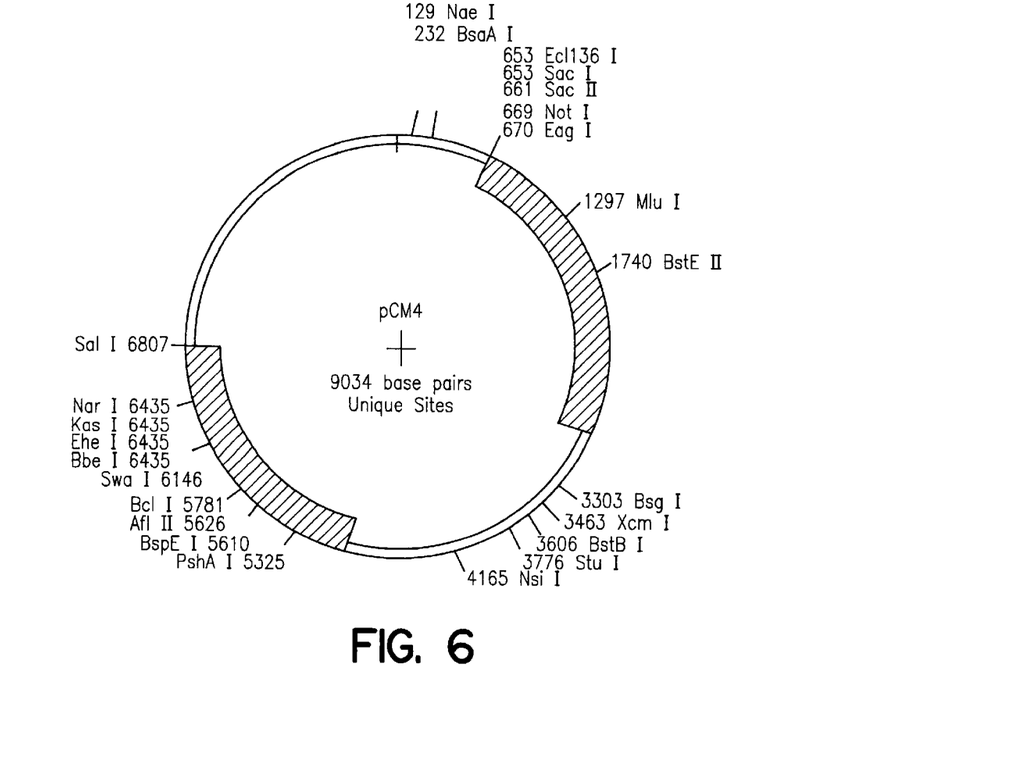
FIG. 6: Plasmid pCM4

The plasmid pCM1 is digested with AvrII and HpaI so as to eliminate part of the ERG4 ORF and the PDR1 ORF which will be replaced by the disruption cassette. The different restriction fragments are separated by electrophoresis on a 0.8% agarose gel. The 6302 bp fragment is then electroeluted and purified by extraction with a phenol-chloroform mixture. The plasmid pDIS4 is digested with XbaI and Ecl136II to obtain the compatible disruption cassette. The different restriction fragments are separated by electrophoresis on a 0.8% agarose gel. The 2725 bp fragment is then electroeluted and purified by extraction with a phenol-chloroform mixture. The two fragments thus prepared are ligated together. After transformation of E. coli, the plasmid called pCM4 (cf. FIG. 6) allowing the disruption of the ERG4 and PDR1 genes is prepared. It is finally digested with SacI and SalI. The linear fragment thus obtained is electroeluted and purified by extraction with a phenol-chloroform mixture, for the purpose of the transformation allowing the disruption of the ERG4 and PDR1 genes.

c) Construct allowing the disruption of the PDR1 gene

Figure 7:
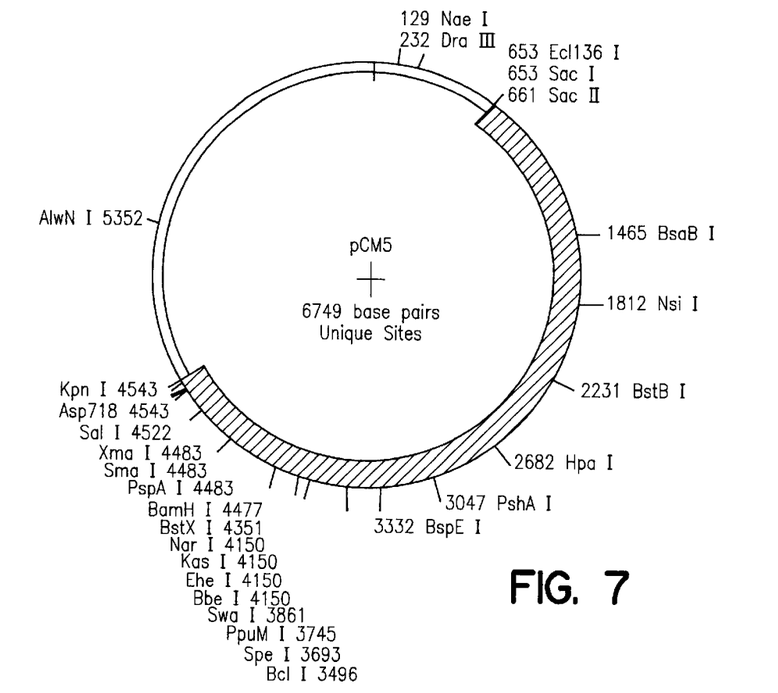
FIG. 7: Plasmid pCM5
Figure 8:
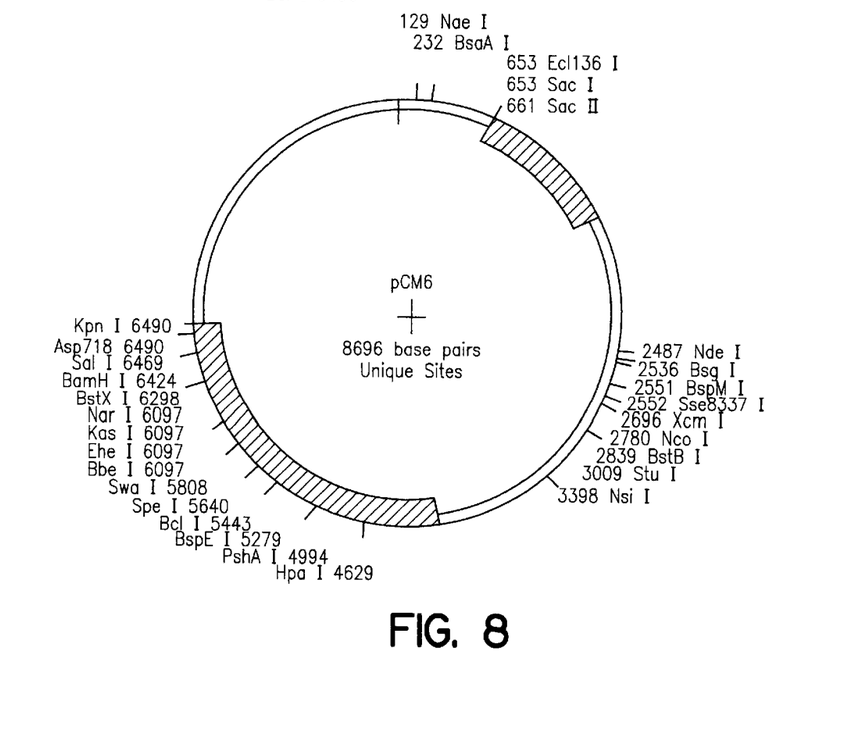
FIG. 8: Plasmid pCM6

The plasmid pCM1 is digested with SacII and then extracted with a phenol-chloroform mixture and finally religated so as to eliminate a DNA fragment which is disruptive for the construct allowing the disruption of the PDR1 gene. After transformation of E. coli, the plasmid having eliminated the 2854 bp fragment is obtained and designated pCM5 (cf. FIG. 7). This plasmid is then digested with BstBI and BsaBI. The different restriction fragments are separated by electrophoresis on a 0.8% agarose gel. The 5983 bp fragment is then electroeluted and extracted with a phenol-chloroform mixture. The plasmid pDIS3 is digested with ClaI and Ecl136II. The different restriction fragments are separated by electrophoresis on a 0.8% agarose gel. The 2709 bp fragment is then electroeluted and extracted with a phenol-chloroform mixture. The two fragments thus prepared are ligated together. After transformation of E. coli, the plasmid allowing the disruption of the PDR1 gene, called pCM6 (cf. FIG. 8) is prepared. It is finally digested with SalI and SacI. The linear fragment thus obtained is electroeluted and purified by extraction with a phenol-chloroform mixture, for the purpose of the transformation allowing the disruption of the PDR1 gene.

3) Transformation of the yeast.

The strain of yeast used is the strain S. cerevisiae 5247 (Marcireau, 1992) of the ura3, trp1, MAT α genotype. This strain is transformed according to the method described by Gietz (Gietz, 1992).

The clones which have integrated the disruption cassette are selected for their prototrophy for uracil. After having checked that the integration occurred at the locus (production of the expected phenotype), the URA3 cassette is lost after subculturing on complete medium. The clones which have lost the URA3 cassette by recombination of the two repeat sequences are selected on a medium containing 10 mM 5-fluoroorotate.

4) Production of the yeast strains possessing the modified PDR1, ERG4 and PDR1-ERG4 genes.

The strain 5247 is transformed as described in 3) with the fragments prepared as described in 2a), 2b), 2c). After elimination of the selectable marker, the strains yCM30 (Δpdr1, ura3, trp1, MAT α), yCM63 (Δerg4, ura3, trp1, MAT α) and yCM65 (Δpdr1, Δerg4, ura3, trp1, MAT α) are obtained.

EXAMPLE 2

Evaluation of the permeability of the yeast obtained according to Example 1

The permeability of the yeasts obtained in Example 1 is determined by measuring the sensitivity to different cytotoxic products. The different yeasts are inoculated at an optical density of 0.05 to 700 nm in YNB minimum medium correctly supplemented with bases and amino acids in the presence of an increasing concentration of xenobiotics. The cultures are placed at 28° C. and at 200 rpm for 48 hours. The optical density at 700 nm is then measured. The $EC_{50}$ is then determined as the xenobiotic concentration inhibiting the growth of the yeast by half compared with a control without xenobiotic.

Table I below presents the results obtained.

EXAMPLE 3

Preparation of the strains possessing inactivated ERG6 and ERG6-PDR1.

1) Production of the constructs allowing the disruption of the ERG6 and ERG6, PDR1 genes.

a) Construct allowing the disruption of the ERG6 gene

Figure 9:
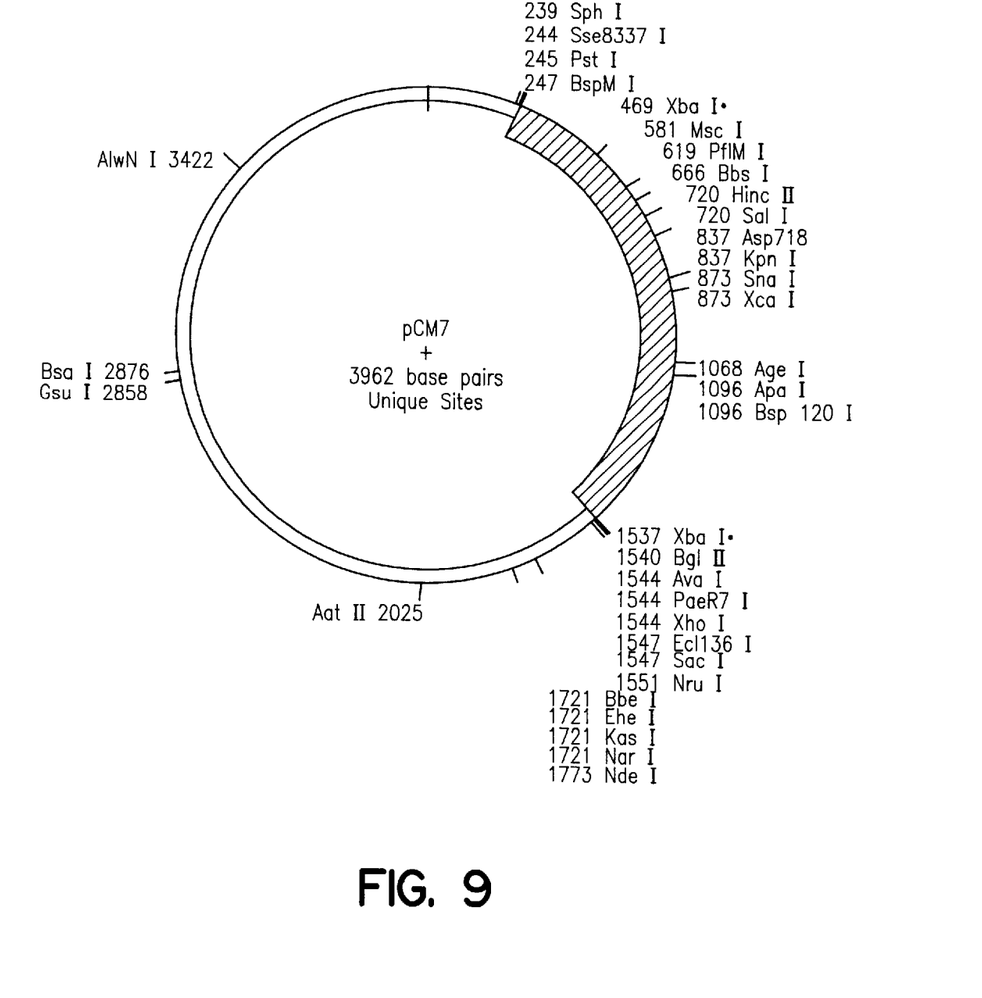
FIG. 9: Plasmid pCM7
Figure 10:
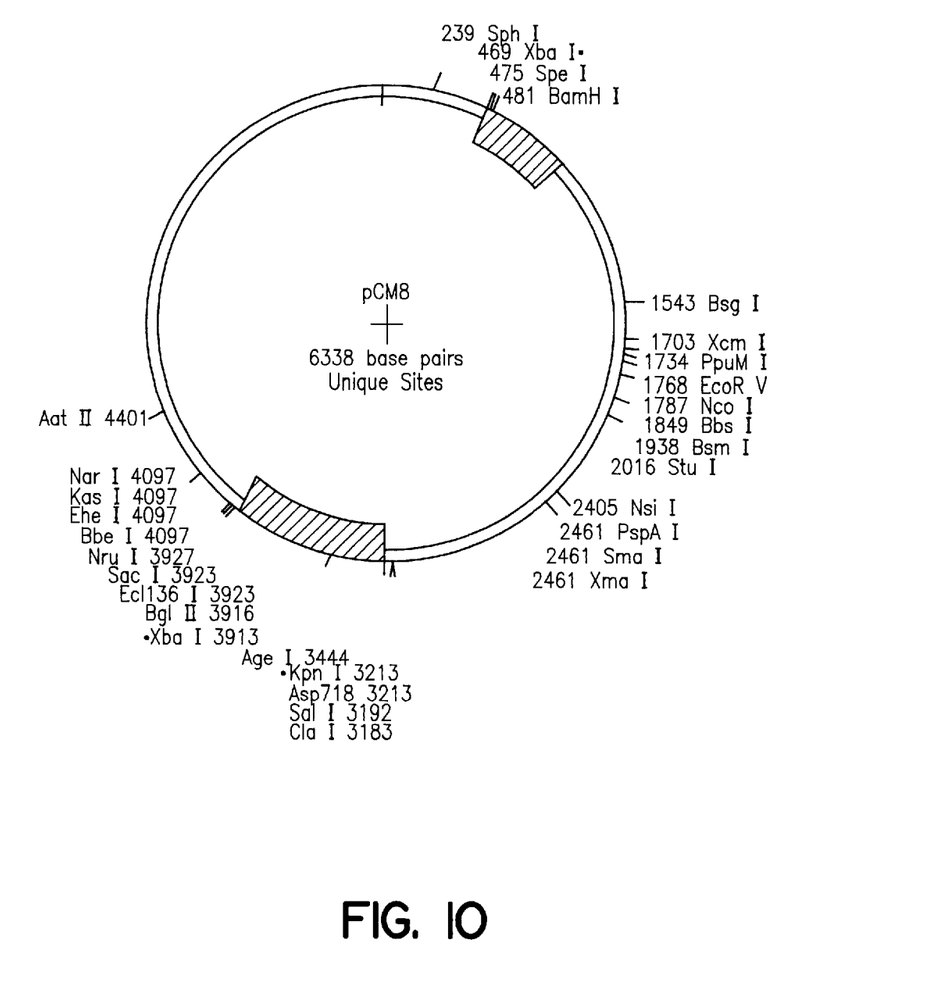
FIG. 10: Plasmid pCM8

The ERG6 gene is obtained by PCR in order to introduce suitable restriction sites. The primers used are TTA CTT TCG ATT TAA GTT TTA CAT AAT TTA AAA SEQ ID No. 1 for the 5' edge and GGC CTG CTC ATG AAC GTG CTA TCT T SEQ ID No. 2 for the 3' edge. The temperature programme for the PCR is the following: 2 minutes at 91° C., then 30 cycles of one minute at 91° C., then 2 minutes at 45° C. and 3 minutes at 72° C. and finally 5 minutes at 72° C. The PCR product after electrophoresis on a 0.8% agarose gel is electroeluted and extracted with a phenol-chloroform mixture. It is then digested with DraI and XhoI whereas the pIC20H is digested with EcoRV and XhoI. After electrophoresis on a 0.8% agarose gel, the two fragments are electroeluted and extracted with a phenol-chloroform mixture and ligated together. After transformation of E. coli, the plasmid called pCM7 (cf. FIG. 9) is prepared from the colonies obtained. The latter is digested with XbaI and KpnI. The different restriction fragments are separated by electrophoresis on a 0.8% agarose gel. The 3594 bp fragment is then electroeluted and extracted with a phenol-chloroform mixture. The plasmid pDIS1 is digested with XbaI and KpnI. The different restriction fragments are separated by electrophoresis on a 0.8% agarose gel. The 2744 bp fragment is then electroeluted and extracted with a phenol-chloroform mixture. The two fragments thus prepared are ligated together. After transformation of E. coli, the plasmid pCM8 is obtained (cf. FIG. 10). For the disruption of ERG6, it is finally digested with BamHI and BglII. The linear fragment thus obtained is electroeluted and purified by extraction with a phenol-chloroform mixture, for the purpose of the transformation allowing the disruption of the ERG6 gene.

2) Transformation of the yeast

A yeast is transformed according to the procedure described in Example 1.3).

3) Production of the strains deleted for ERG6 and ERG6, PDR1

The strain 5247 is transformed by the fragment prepared as described in 1a. After elimination of the selectable marker, the strain yCM55 (Δerg6, ura3, trp1, MAT α) is obtained.

The strain yCM30 is transformed by the fragment prepared as described in 1a. After elimination of the selectable marker, the strain yCM57 (Δpdr1, Δerg6, ura3, trp1, MAT α) is obtained.

EXAMPLE 4

Evaluation of the permeability of the yeast strains yCM30, yCM55, yCM57.

This evaluation was carried out according to the procedure described in Example 2. The corresponding results are presented in Table II.

EXAMPLE 5

Preparation of the yeast strains possessing inactivated PDR5 and SNQ2

1) Production of the constructs allowing the disruption of the PDR5 and SNO2 genes.

a) Disruption of the PDR5 gene

Figure 11:
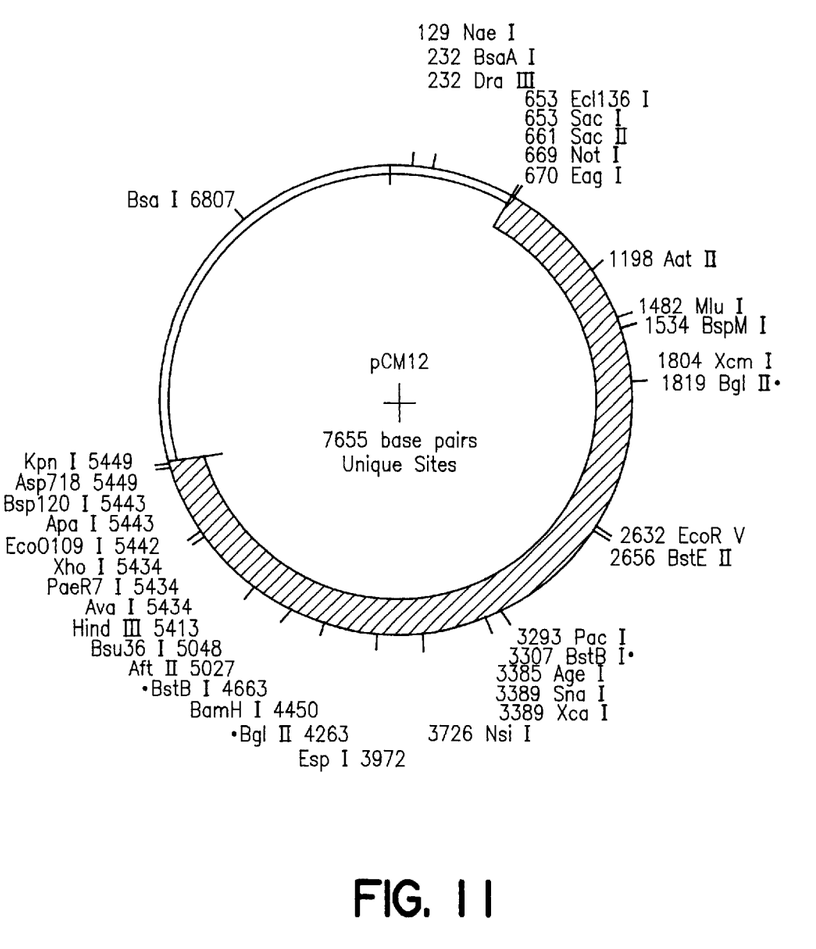
FIG. 11: Plasmid pCM12
Figure 12:
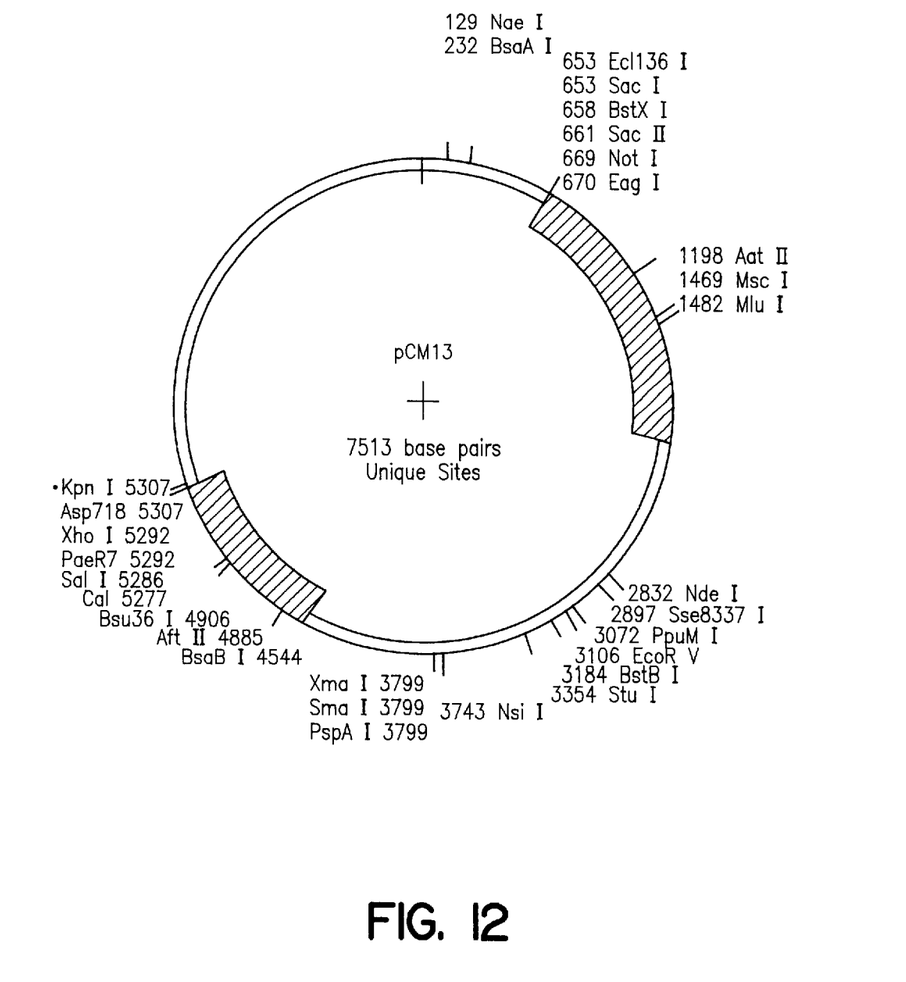
FIG. 12: Plasmid pCM13

The 4736 bp AvrII-HindIII DNA fragment (comprising part of the PDR5 ORF), of the plasmid pDR3.3 (Leppert 90) whose sequence is deposited in the EMBL data bank under the reference L19922 is ligated into the plasmid Bluescript II (ks) preferably digested. with HindIII and XbaI. After transformation of E. coli, the plasmid called pCM12, having the insert, is selected (cf. FIG. 11). This plasmid is then digested with BstBI and BglII. The different restriction fragments are separated by electrophoresis on a 0.8% agarose gel. The 4811 bp fragment is then electroeluted and extracted with a phenol-chloroform mixture. The plasmid pDIS4 is digested with ClaI and BamHI. The different restriction fragments are separated by electrophoresis on a 0.8% agarose gel. The 2702 bp fragment is then electroeluted and extracted with a phenol-chloroform mixture. The two fragments thus prepared are ligated together. After transformation of E. coli, the plasmid called pCM13, allowing the disruption of PDRS, is prepared (cf. FIG. 12). It is finally digested with ClaI and SacI. The linear fragment thus obtained is electroeluted and purified by extraction with a phenol-chloroform mixture, for the purpose of the transformation allowing the disruption of the PDR5 gene.

b) Disruption of the SNQ2 gene

Figure 13:
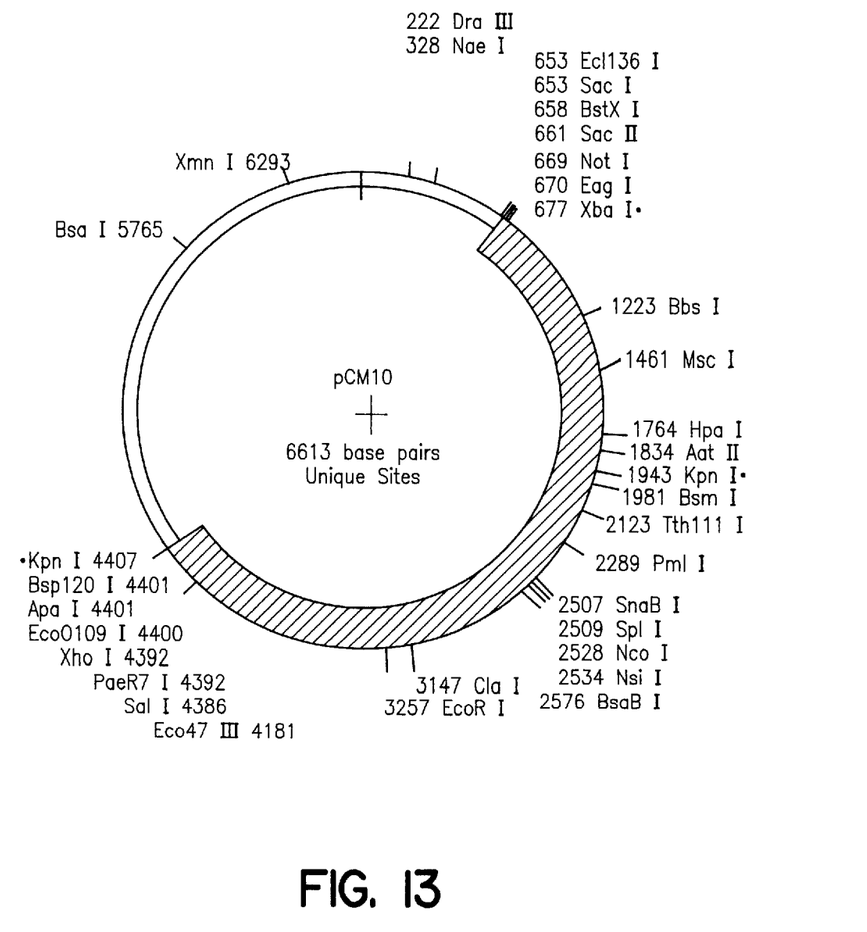
FIG. 13: Plasmid pCM10
Figure 14:
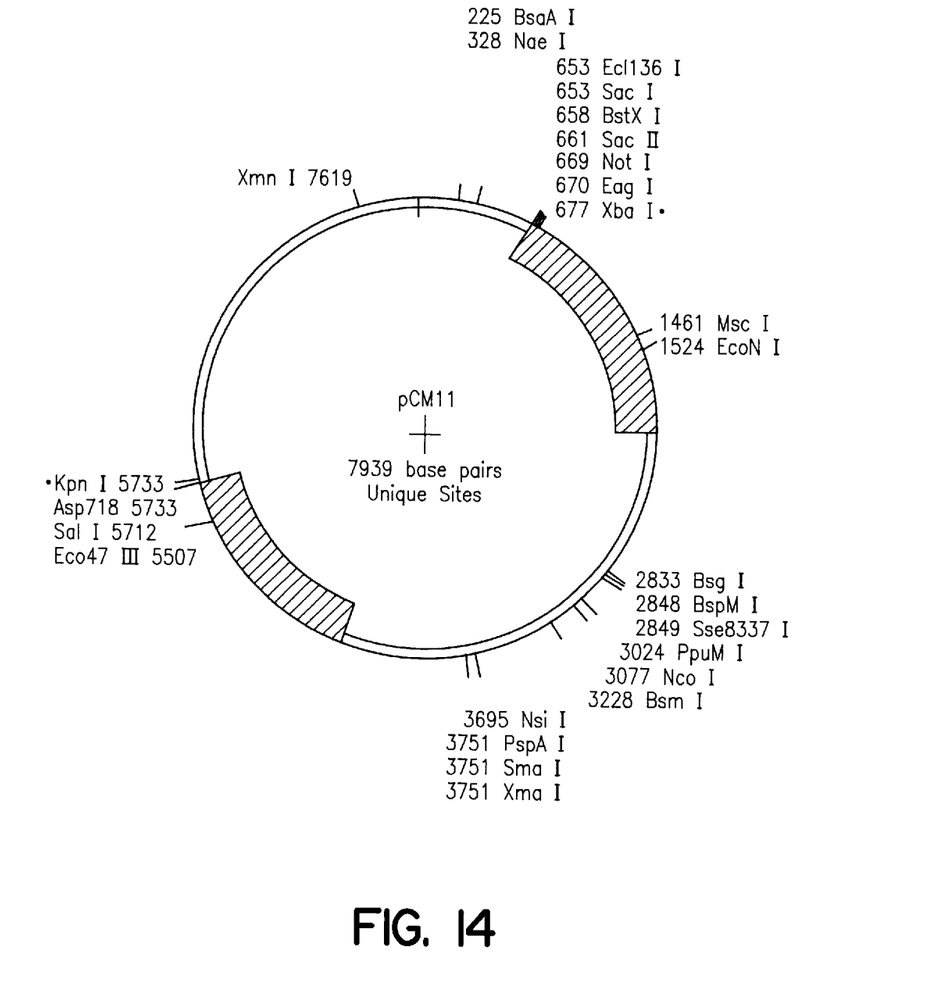
FIG. 14: Plasmid pCM11

The 3688 bp NarI-BglII DNA fragment (comprising part of the SNQ2 ORF) of the plasmid pEH5222 (Servos 1993) whose sequence is deposited in the EMBL data bank under the reference X66732, is ligated into the plasmid Bluescript II (ks-) previously digested with BamHI and ClaI. After transformation of E. coli, the plasmid called pCM10, possessing the insert is selected (cf. FIG. 13). This plasmid is then digested with ClaI and HpaI so as to eliminate part of the SNQ2 ORF which will be replaced by the disruption cassette. The different restriction fragments are separated by electrophoresis on a 0.8% agarose gel. The 5230 bp fragment is then electroeluted and purified by extraction with a phenol-chloroform mixture. The plasmid pDIS3 is digested with ClaI and Ecl136II in order to obtain the compatible disruption cassette. The different restriction fragments are separated by electrophoresis on a 0.8% agarose gel. The 2709 bp fragment is then electroeluted and purified by extraction with a phenol-chloroform mixture. The two fragments thus prepared are ligated together. After transformation of E. coli, the plasmid called pCM11 (cf. FIG. 14) allowing the disruption of SNQ2, is prepared. It is finally digested with XbaI and SalI. The linear fragment thus obtained is electroeluted and purified by extraction with a phenol-chloroform mixture, for the purpose of the transformation allowing the disruption of the SNQ2 gene.

2) Production of the strains deleted for PDR5 and SNQ2

The strain 5247 is transformed by the fragment prepared as described in 1a and 1b. After elimination of the selectable marker, the strain yCM33 (Δpdr5, ura3, trp1, MAT α) and the strain yCM67 (Δsng2, ura3, trp1, MAT α) are obtained.

3) Production of the strains deleted for PDR1, PDR5, SNQ2 and ERG6

The strain yCM30 is transformed by the fragment prepared as described in Example 5 in 1a. After elimination of the selectable marker, the strain yCM45 (Δpdr1, Δpdr5, ura3, trp1, MAT α) is obtained. The strain yCM45 is transformed by the fragment prepared as described in Example 5 in 1b. After elimination of the selectable marker, the strain yCM51 (Δpdr1, Δpdr5, Δsnq2, ura3, trp1, MAT α) is obtained. The strain yCM51 is transformed by the fragment prepared as described in Example 1 in 1a. After elimination of the selectable marker, the strain yCM61 (Δpdr1, Δpdr5, Δsnq2, Δerg6, ura3, trp1, MAT α) is obtained.

EXAMPLE 6
Evaluation of the permeability of the yeast strain obtained in Example 5

The permeability of the yeast strains 5247 and yCM61 is determined by measurement of the sensitivity to different cytotoxic products. The different yeasts are inoculated at an optical density of 0.05 to 700 nm in YNB minimum medium correctly supplemented with bases and amino acids in the presence of an increasing concentration of xenobiotics. The cultures are placed at 28° C. and at 200 rpm for 48 hours. The optical density at 700 nm is then measured. The $EC_{50}$ is determined as the xenobiotic concentration inhibiting the growth of the yeast by half compared with a control without xenobiotic.

Table III below presents the results obtained.

TABLE I

| STRAIN | DOXORUBICIN $EC_{50}$ ($\mu M$) | RATIO | ACTINOMYCIN D $EC_{50}$ ($\mu M$) | RATIO | CYCLO-HEXIMIDINE $EC_{50}$ ($\mu M$) | RATIO |
|---|---|---|---|---|---|---|
| 5247 (wt) | 40.5 | 1 | 23.9 | 1 | 53 | 1 |
| yCM63 (Δerg4) | 9.2 | 4.4 | 6.4 | 3.7 | — | — |
| yCM30 (Δpdr1) | 18.4 | 2.2 | 12.7 | 1.9 | 2.5 | 21.2 |
| yCM65 (Δpdr1, Δerg4) | 5.15 | 7.8 | 5.8 | 4.1 | 0.5 | 106 |

TABLE II

| STRAIN | DOXORUBICIN $EC_{50}$ ($\mu M$) | RATIO | ACTINOMYCIN D $EC_{50}$ ($\mu M$) | RATIO | CYCLO-HEXIMIDINE $EC_{50}$ ($\mu M$) | RATIO |
|---|---|---|---|---|---|---|
| 5247 (wt) | 40.5 | 1 | 23.9 | 1 | 53 | 1 |
| yCM55 (Δerg6) | 12 | 3.4 | 5.6 | 4.3 | 2.3 | 23 |
| yCM30 (Δpdr1) | 18.4 | 2.2 | 12.7 | 1.9 | 2.5 | 21.2 |
| yCM57 (Δpdr1, Δerg6) | 1.7 | 23.8 | 0.75 | 31.9 | 0.2 | 265 |

TABLE III

| COMPOUND | 5247 (wt) $EC_{50}$ ($\mu M$) | yCM61 (Δpdr1, Δpdr5, Δsnq2, Δerg6) $EC_{50}$ ($\mu M$) | RATIO |
|---|---|---|---|
| Novobiocin | 245 | 9 | 27 |
| Lovastatin | 143 | 3.8 | 37 |
| Sulphomethuron | 6.9 | 0.13<< | >>50 |
| Camptothecin | >>574 | 5.74 | >>100 |
| Cycloheximide | 71 | 0.142 | 500 |

BIBLIOGRAPHIC REFERENCES

Al-Fell et al., Proc. Natl. Acad. Sci. USA 1992, 89, 4534,
Anderson et al., J. Biol. Chem. 1989, 264, 19169,
Ashman et al., Lipids 1991, 26, 628,
Arthington et al., Gene 1991, 102, 39,
Ballou 1982, The molecular biology of the yeast Saccharomyces, metabolism and gene expression, eds Cold Spring Harbor Laboratory, 335,
Balzi et al., Biochim, Biophys. Acta 1991, 1073, 241,
Basson et al., Proc. Natl. Acad. Sci. USA 1986, 53, 5563,
Boone et al., J. Cell. Biol. 1990, 110, 1833,
Brown et al., Genetics 1993, 133, 837,
Chen et al., Curr. Genet. 1987, 12, 185,
Dean-Johnson et al., J. Biol. Chem. 1989, 264, 1274,
Dequin et al., Cur. genet. 1988, 13, 471,
Dexter et al., Genetics 1994, 136, 505,
Gietz et al., Nucl. Acids Res. 1992, 20, 1425,
Fegueur et al., Cur. Genet 1991, 20, 365,
Hara et al., Proc. Natl. Acad. Sci. USA 1993, 90, 2281,
Hardwick et al., Yeast 1994, 10, 265,
Hill et al., Genetics 1992, 130, 273,
Hjelmstad et al., J. Biol. Chem. 1991, 266, 4357,
Hoegenauer et al., Gene 1991, 107, 155,
Hosaka et al., J. Biol. Chem. 1989, 264, 2053,
Hutchins et al., J. Bacteriol, 1983, 154, 161,
Kalb et al., DNA 1987, 6, 529,
Kanawaza et al., Mol. Cell. Biol. 1988, 8, 664,
Kanik et al., Mol. Cell. Biol. 1990, 10, 898,
Karst et al., Molec. Gen. Genet 1977, 154, 269,
Kiyono et al., J. Biochem 1987, 102, 1089,
Klis, Yeast 1994, 10, 851,
Kodaki et al., J. Biol. Chem. 1987, 262, 15428),
Kodaki et al., J. Biochem 1991, 109, 276,
Kuchler et al., EMBO J. 1989, 8, 3973,
Lai et al., Gene 1994, 140, 41,
Lee et al., biosciences biotechnology and biochemistry, 1994, 58, 391,
Leppert et al., Genetics 1990, 125, 30,
Lussier et al., Yeast 1993, 9, 1057,
Marcireau et al., Cur. Genet. 1992, 22, 267,
Marsh et al. Gene 32 (1984) 481,
Meader et al., Mol Cell. Biol. 1990, 10, 3013,
Meyers et al., Curr. Genet. 1992, 21, 431,
Mohamed et al., J. Biol. Chem. 1990, 263, 12315,
Molzhan et al., J. Gen. Microbiol 1972, 72, 339,
Mons, Doctorate Thesis, University of Poitiers 1984,
Moye-Rowley et al., Genes and development 1989, 3, 283,
Nikawa et al., J. Biol. Chem. 1987, 262, 4876,
Oulmouden et al., Gene 88, 253,
Renaud et al., Eur. J. Biochem., 1990, 194, 889
Roemer et al., Proc. Natl. Acad. Sci. USA 1991, 88, 11295,
Rothstein Meth. Enzymol. 101 (1983) 202,
Sawadogo and Van Dyke, Nucleic- Acids Res. 19 (1991) 674,
Schwezer et al., Molec. Gen. Genet. 1986, 203, 481,
Servos et al., Mol. Gen. Genet. 1993, 236, 214,
Servouse et al., Biochem. Biophys. Res. Commun. 1984, 123, 424,
Shimizu et al., Mol. Gen. Genet. 1994, 242, 641,
Sinha et al., Nucleic Acids Res. 12 (1984) 4539,
Stateva et al., Mol. Cell. Biol. 1991, 11, 4235,
Stukey et al., J. Biol. Chem. 1990, 265, 20144,
Tsay et al., Mol. Cell. Biol. 1991, 11, 620,
Tsukagoshi et al., Eur. J. Biochem. 1987, 169, 477,
Yabusaki, The international review of pharmaceutical technology research and development, 1992, 163.

We claim:

1. A modified yeast in which at least two genes controlling cellular permeability of the said yeast at different levels are inactivated, wherein said different levels are:

a) constitution, biosynthesis or integrity of the cell wall;

b) constitution, biosynthesis or integrity of the plasma membrane; or     c) detoxification or export of endogenous compounds.

2. The modified yeast according to claim 1, wherein at least one of said genes is selected from the group consisting of KRE, KTR, MNN, OCH, CSD, CHS, SKN1, PMR1, PMT1, ERD1, VGR1, VGR4, CAL3, SHC1, DHS1, SRB1, PKC1, BCK1, MKK1, MKK2, MPK1, PPZ1, PPZ2, PMI1, and BGL2.

3. The modified yeast according to claim 1, wherein at least one of said genes is selected from the group consisting of ERG10, ERG11, ERG13, HMG1, HMG2, ERG12, ERG8, ERG19, IDI1, ERG20, ERG9, ERG1, ERG18, ERG7, ERG17, ERG16, ERG24, ERG6, ERG2, ERG3, ERG5, and ERG4.

4. The modified yeast according to claim 1, wherein at least one of said genes is selected from the group consisting of SNQ1, SNQ2, SNQ3, STE6, PDR1, PDR2, PDR3, PDR4, PDR6, PDR7, PDR9, and PDR11.

5. The modified yeast according to claim 1, wherein the genes are inactivated by one or more genetic modifications, and are partially or totally incapable of encoding a natural or active protein.

6. The modified yeast according to claim 1, wherein the inactivated genes encode proteins having decreased function, nonfunctional proteins or proteins having a modified activity spectrum.

7. The modified yeast according to claim 1, wherein said yeast belongs to the genera Saccharomyces, Kluyveromyces, Pichia, Hansenula, Candida or Schyzosaccharomyces.

8. The modified yeast according to claim 1, wherein at least one inactivated gene is involved in detoxification or export of endogenous compounds, and at least one inactivated gene plays a role in the biosynthesis and/or the constitution of the membrane or of the wall of the said yeast.

9. A process for the preparation of a modified yeast according to claim 1, comprising genetic modification of said genes controlling cellular permeability.

10. A process comprising culturing a modified yeast according to claim 1 in the presence of a xenobiotic, and measuring the optical density of the culture to determine an $EC_{50}$ for said xenobiotic.

11. A process for screening biologically active compounds comprising culturing a modified yeast according to claim 1 in the presence of said compound, and measuring the optical density of the culture to determine an $EC_{50}$ for said compound.

12. The modified yeast according to claim 5, wherein the genetic modifications comprise a point mutation, multiple mutations, substitutions, deletions, or additions.

13. The modified yeast according to claim 8, wherein said yeast is a *S. cerevisiae* in which the genes PDR1, PDR5, SNQ2, and EGR6 are modified.

* * * * *